United States Patent [19]

Appelhans et al.

[11] Patent Number: 4,968,888
[45] Date of Patent: Nov. 6, 1990

[54] PULSED FIELD SAMPLE NEUTRALIZATION

[75] Inventors: Anthony D. Appelhans; David A. Dahl; James E. Delmore, all of Idaho Falls, Id.

[73] Assignee: The United States of America as represented by the United States Department of Energy, Washington, D.C.

[21] Appl. No.: 375,442

[22] Filed: Jul. 5, 1989

[51] Int. Cl.$^5$ .............................................. G01N 23/00
[52] U.S. Cl. ................................... 250/306; 250/305; 250/307; 250/309; 250/397; 250/288
[58] Field of Search ............... 250/306, 309, 288, 304, 250/305, 307, 397

[56] References Cited

U.S. PATENT DOCUMENTS

| | | | |
|---|---|---|---|
| 3,628,009 | 12/1971 | Orne et al. | 250/309 |
| 3,889,115 | 6/1975 | Tamura et al. | 250/309 |
| 3,939,344 | 2/1976 | McKinney | 250/309 |
| 4,132,892 | 1/1979 | Wittmaack | 250/309 |
| 4,163,153 | 7/1979 | Tamura et al. | 250/309 |
| 4,455,486 | 6/1984 | Rau | 250/306 |
| 4,556,794 | 12/1985 | Ward et al. | 250/309 |
| 4,680,467 | 7/1987 | Bryson III et al. | |
| 4,710,625 | 12/1987 | Kelly | 250/306 |
| 4,740,697 | 4/1988 | Suzuki | 250/306 |
| 4,818,872 | 4/1989 | Parker et al. | |

Primary Examiner—Jack I. Berman
Assistant Examiner—Kiet T. Nguyen
Attorney, Agent, or Firm—Helen S. Cordell; John M. Albrecht; William R. Moser

[57] ABSTRACT

An apparatus and method for alternating voltage and for varying the rate of extraction during the extraction of secondary particles, resulting in periods when either positive ions, or negative ions and electrons are extracted at varying rates. Using voltage with alternating charge during successive periods to extract particles from materials which accumulate charge opposite that being extracted causes accumulation of surface charge of opposite sign. Charge accumulation can then be adjusted to a ratio which maintains a balance of positive and negative charge emission, thus maintaining the charge neutrality of the sample.

13 Claims, 3 Drawing Sheets

PULSED FIELD SAMPLE NEUTRALIZATION

CONTRACTUAL ORIGIN OF THE INVENTION

The United States Government has rights in this invention pursuant to Contract No. DE-AC07-76ID01570 between the United States Department of Energy and EG&G Idaho, Inc.

BACKGROUND OF THE INVENTION

The present invention relates generally to a novel technique for limiting the accumulation of surface charge on a sample which is being bombarded by a primary beam and from which charged particles are being extracted. More particularly, the present invention relates to a method and apparatus for preventing the accumulation of surface charge beyond a predetermined limit by alternating during successive periods the extraction from the bombarded surface of charge of opposite signs.

Surface analysis of a material sample by processes such as secondary ion mass spectrometry (SIMS), Auger electron spectroscopy (AES) or their equivalents involve bombarding a sample with a primary beam and removing charged particles from the sample.

Secondary ion mass spectrometry involves bombarding a sample material with a high energy primary beam of neutral and/or charged particles (positive or negative ions, atoms or molecules). These particles impact the surface of the sample causing the emission of secondary neutral and charged particles (e.g. electrons, positive and negative ions, atoms, and molecules) some of which are subsequently mass analyzed to determine the composition of the sample. Similarly, AES involves bombarding the surface of a sample with high energy electrons which then result in the emission of Auger electrons, which are then energy analyzed to provide information on the composition of the sample.

If the net flux of positive and negative charges, i.e. ions and electrons, entering and leaving the sample is not perfectly balanced the sample will tend to become charged. Sample charging can destroy primary beam characteristics, interfere with the extraction of charged particles, and shift the energy of the extracted charged particles, making analysis difficult or impossible.

In electrically conducting samples charge accumulation may be prevented by electrically grounding the sample. The ground assures that the net charge flux of the sample will always be zero and, consequently, no charge accumulation will occur. Preventing or limiting charge accumulation in electrically non-conducting or poorly conducting materials (such as polymers, ceramics, glasses, and biospecimens) presents a more difficult problem.

The charge cycles commonly encountered during SIMS analysis of an electrically nonconducting sample exemplify the conditions toward which the present invention is directed:

(a) The most common mode of SIMS analysis is to use a primary beam of positive ions which results in emission of secondary positive and negative ions and secondary electrons from the sample. For known materials, the positive primary beam creates fewer secondary positive ions than primary ions. Use of an electric field of negative potential to extract positive secondary ions consequently causes the sample to accumulate a positive charge. Use of an electric field of positive potential to extract negative secondary ions and electrons causes the sample to accumulate a positive charge at an even greater rate.

(b) A neutral primary beam for SIMS analysis causes charge accumulation at a rate that is significantly less than that of the positive primary beam, but the imbalance between positive ion and negative ion and electron production and extraction can still cause charge accumulation on the sample.

(c) A negative primary ion beam has been used for SIMS analysis to create positive and negative secondary ions. Extraction of positive secondary ions will cause the sample to accumulate negative charge. Charge accumulation on the sample due to extraction of negative secondary ions will depend upon the material and bombardment energy. The secondary negative charge yield under keV energy negative ion primary bombardment is greater than the charge flux of the primary beam for many materials. Extraction of negative particles will cause such materials to accumulate positive charge.

In the prior art, conducting grids and electron flooding have been used to reduce accumulation of positive charge in non-conducting samples during SIMS analysis.

U.S. Pat. No. 4,680,467 issued July 14, 1987, to Bryson III et. al. discloses the use of an electrically conductive grid comprised of intersecting wires or vanes positioned in closely spaced relationship to the surface of the sample for smoothing the gradients in the electrical potential in the region of the beam spot during electron spectroscopy. However, conducting grids are known to add a background signal to the mass spectrum of the sample. In addition, conducting grids have a high probability of introducing contaminants to the surface of the sample and may cause chemical changes in the surface of the sample.

U.S. Pat. No. 4,818,872 issued Apr. 4, 1989, to Parker et al. discloses an electron gun which floods the sample with low energy electrons neutralizing charge accumulation. Electron flood guns are effective in many cases but may damage the sample, particularly polymers. Electron stimulated desorption and resulting noise may also be caused by electron flood guns.

Therefore, in view of the above, it is an object of the present invention to provide an apparatus and method for maintaining a neutral surface potential for a sample of electrically nonconducting or poorly conducting material that is being analyzed by a method causing extraction of charged particles from the sample.

It is another object of the present invention to provide a non-intrusive apparatus and method for maintaining a neutral surface potential so that sample integrity is maintained.

A yet further object of this invention is to present a method for limiting surface charge accumulation within predetermined values.

It is another important object of this invention to present an apparatus and method which enables the near simultaneous collection of both positive and negative secondary ion spectra.

Additional objects, advantages and novel features of the invention will be set forth in part in the description which follows and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects this invention comprises an apparatus and method for alternating voltage and for varying the rate of extraction during the extraction of secondary particles, resulting in periods when either positive ions, or negative ions and electrons are extracted at varying rates. Using voltage with alternating charge during successive periods to extract particles from materials which accumulate charge opposite that being extracted causes accumulation of surface charge of opposite sign. Charge accumulation can then be adjusted to a ratio which maintains a balance of positive and negative charge emission, thus maintaining the charge neutrality of the sample.

In addition, surface charge accumulation can be limited within predetermined values by determining the rate of charge accumulation for the sample material under the conditions of primary beam bombardment, and varying the length of time for which particles of each charge sign are extracted.

Many materials exhibit the characteristics necessary for the method of the present invention to be effective for one or more primary beams and energies but not all. Many important materials have been shown to exhibit the necessary charge accumulation characteristics for neutral or negative primary beams.

This method is compatible with many types of apparatus that extract charged particles for analysis. Apparatus which can alternate the charge of the particles extracted and the periods during which particles are extracted may implement the method of the present invention.

BRIEF DESCRIPTION OF THE DRAWINGS

The accompanying drawings which are incorporated in and form part of the specification, illustrate an embodiment of the present invention and together with the description serve to explain the principles of the invention in the drawings.

DETAILED DESCRIPTION OF THE INVENTION

Figure 1:
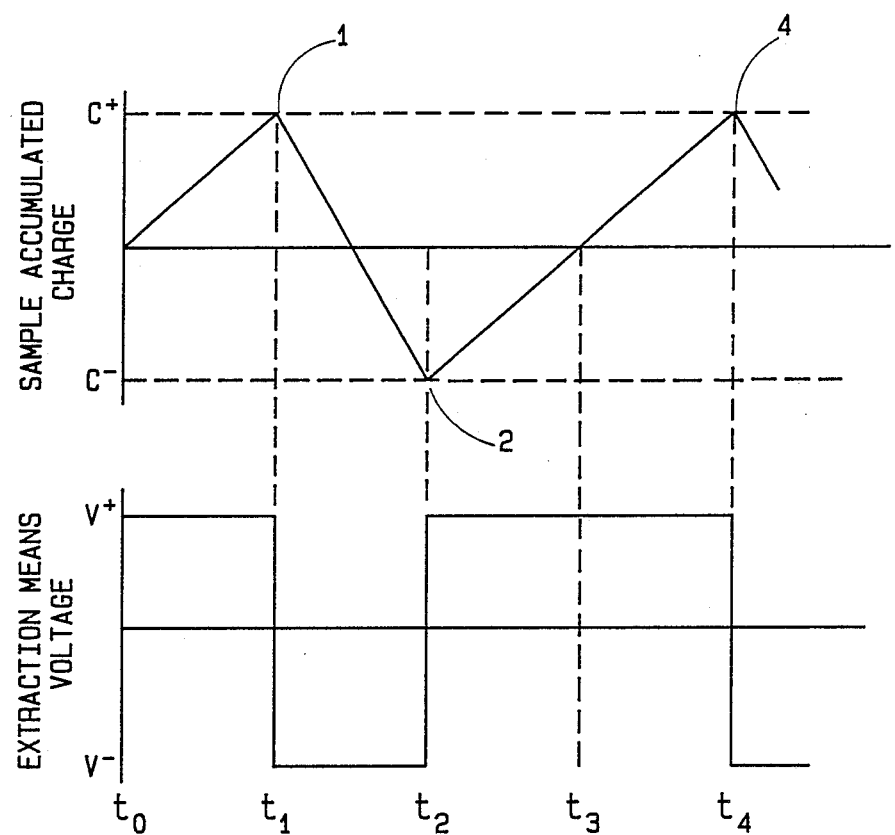
FIG. 1 is a graph illustrating the relationship between a square wave voltage which can be used to alternate the charge of ion extraction fields in accordance with the present invention and the sample charge accumulation which may result.

The present invention is based on causing a sample to alternately accumulate positive and negative charge, or to alternately increase or decrease the rate of charge extraction, thereby limiting the maximum accumulated net charge. The invention, sample materials for which the present invention is applicable, and parameters which must be specified to practice the invention may best be understood from the expression for sample charge accumulation rate in terms of charge fluxes:

$$\frac{dQ_s}{dt} = (J_{out}^- - J_{in}^-) - (J_{out}^+ - J_{in}^+) \tag{1}$$

where $Q_s$ is sample surface charge, and J is the magnitude of the charge flux of sign indicated by the superscript and direction indicated by the subscript. For a nonconducting or poorly conducting sample, flux into the sample is due only to the primary beam and flux out is due only to secondary particle extraction. The conditions which must be met for practice of the invention may be understood by considering the effects of each type of primary beam:

(a) A neutral primary beam causes no charge flux into a sample, i.e. $J_{in}^- = J_{in}^+ = 0$. For extraction of positive secondary particles, $J_{out}^- = 0$ and $J_{out}^+ > 0$. Equation 1 gives:

$$\frac{dQ_s}{dt} = -J_{out}^+ < 0 \tag{2}$$

indicating accumulation of negative charge. For extraction of negative secondary particles, $J_{out}^- > 0$ and $J_{out}^+ = 0$, and Equation 1 gives:

$$\frac{dQ_s}{dt} = J_{out}^- > 0 \tag{3}$$

indicating accumulation of positive charge. Equations 2 and 3 demonstrate that any material from which both positive and negative particles can be extracted during bombardment by a neutral primary beam can be caused to accumulate positive or negative charge.

(b) A negative primary beam creates only a negative charge flux into a sample, i.e. $J_{in}^- > 0$ and $J_{in}^+ = 0$. For extraction of positive secondary particles, $J_{out}^- = 0$ and $J_{out}^+ > 0$ Equation 1 gives:

$$\frac{dQ_s}{dt} = -J_{in}^- - J_{out}^+ < 0 \tag{4}$$

indicating accumulation of negative charge. For extraction of negative secondary particles, i.e. $J_{out}^- > 0$, $J_{out}^+ = 0$, Equation 1 gives:

$$\frac{dQ_s}{dt} = J_{out}^- - J_{in}^- \tag{5}$$

Equation 5 indicates that positive charging of a sample can occur for a negative primary beam only for materials and primary beams for which:

$$J_{out}^- > J_{in}^- \tag{6}$$

Because as demonstrated by Equation 4, negative charging always occurs for positive secondary particle extraction and a negative primary beam, Equation 6 is the condition which must be satisfied for the present invention to function successfully for a negative primary beam.

(c) A positive primary beam creates only a positive charge flux into a sample, i.e. $J_{in}^- = 0$ and $J_{in}^+ > 0$. For extraction of negative particles, $J_{out}^+ = 0$ and $J_{out}^- > 0$, Equation 1 gives:

$$\frac{dQ_s}{dt} = J_{out}^- + J_{in}^+ > 0 \quad (7)$$

indicating accumulation of positive charge. For extraction of positive particles, $J_{out}^- = 0$ and $J_{out}^+ > 0$, Equation 1 gives:

$$\frac{dQ_s}{dt} = J_{in}^+ - J_{out}^+ \quad (8)$$

Equation 8 indicates that negative charging of a sample can occur for a positive primary beam only for materials and primary beams for which:

$$J_{out}^+ > J_{in}^+ \quad (9)$$

Because, as demonstrated by Equation 7, positive charging always occurs for a positive primary beam and negative particle extraction Equation 9 is the condition which must be satisfied for the present invention to function successfully for a positive primary beam.

Secondary particles may be extracted by creating an electric field adjacent to the sample surface that will extract secondary charged particles of the desired charge sign. FIG. 1 illustrates the relationship between voltage applied as a means to create an extraction field and sample charge accumulation. The sign of the charge accumulation rate on the sample changes when the sign of the secondary particles being extracted changes at times $t_1$, $t_2$, and $t_4$, indicated at points designated 1, 2, and 4, respectively, in FIG. 1. The periods of time during which secondary particles of each charge sign are extracted are determined for each sample, primary beam and extraction apparatus to be that which will cause the sample charge to change from one acceptable level to another, the periods from $t_1$ to $t_2$, and from $t_2$ to $t_4$ of FIG. 1. There is no net accumulation of charge after successive extractions of secondary particles of opposite sign, or, referring to FIG. 1, $$\int_{t_1}^{t_4} \frac{dQ_s}{dt} dt = 0.$$

Substituting the relationship of Equation 1, $$\int_{t_1}^{t_4} \frac{dQ_s}{dt} dt = \int_{t_1}^{t_2} [(J_{out}^- - J_{in}^-) - (J_{out}^+ - J_{in}^+)] dt + \quad (10)$$

$$\int_{t_2}^{t_4} [(J_{out}^- - J_{in}^-) - (J_{out}^+ - J_{in}^+)] dt = 0$$

where the charge flux integral has been divided into periods of positive and negative secondary particle extraction. The relationships for a given primary beam may be substituted into Equation 10. As an example, substituting the relations of Equations 2 and 3 for a neutral primary beam into Equation 10 gives, $$\int_{t_1}^{t_4} \frac{dQ_s}{dt} dt = \int_{t_1}^{t_2} -J_{out}^+ dt + \int_{t_2}^{t_4} J_{out}^- dt = 0 \quad (11)$$

Assuming that the charge fluxes are constant over these time periods gives $$J_{out}^-(t_4-t_2) - J_{out}^+(t_2-t_1) = 0 \quad (12)$$

Equation 12 gives the relationship between time periods from $t_1$ to $t_2$ and from $t_2$ to $t_4$ in terms of extraction charge flux. The periods can be determined from the relation $$(C^- C^+) = -J_{out}^+(t_2-t_1) \quad (13)$$

Equations 1 through 13 illustrate the relationships which govern the present invention. The values that are used for maximum acceptable charge accumulation, $C^+$ and $C^-$ and charge flux magnitudes $J_{in}^-$, $J_{out}^-$, $J_{in}^+$, $J_{out}^+$, are dependent on the primary beam, sample material, and extraction method. The extraction means voltage and charge accumulation of FIG. 1 are illustrative of the method. Functions other than a square wave may be used for extraction means voltage and charge accumulation may be other than linear. For purposes of this embodiment it is necessary only that charge accumulation of both signs occur.

Figure 2:
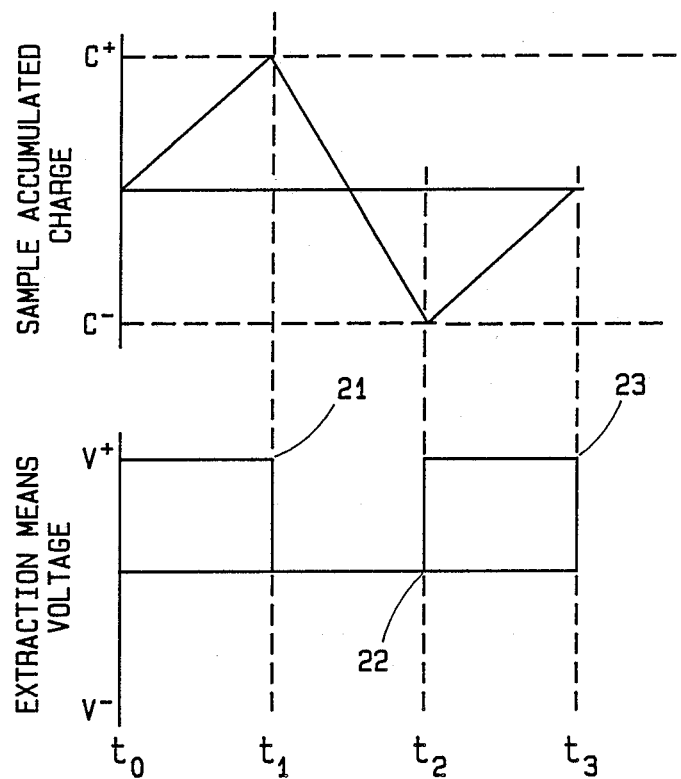
FIG. 2 is a graph illustrating a square wave voltage which can be used to vary the rate of ion extraction while allowing the sign of the charge accumulation to remain unchanged.

FIG. 2 illustrates an embodiment of the invention in which a square wave voltage can be used to vary the rate of charged particle extraction while allowing the sign of the charge accumulation to remain unchanged. The rate of charge accumulation on the sample changes at times $t_1$, $t_2$, and $t_3$, indicated by numerals 21, 22, and 23 respectively in FIG. 2. The ragtes of extraction and the periods of time during which secondary particles are extracted at the predetermined rates are determined for each sample, primary beam and extraction apparatus to be those which will cause the sample charge to change from one acceptable level to another during the periods from $t_1$ to $t_2$, and from $t_2$ to $t_3$ of FIG. 2. There is no net accumulation of charge after successive extractions of secondary particles at the predetermined rates, or, referring to FIG. 2, $$\int_{t_1}^{t_3} \frac{dQ_s}{dt} dt = 0$$

Substituting the relationship of Equation 1, $$\int_{t_1}^{t_3} \frac{dQ_s}{dt} dt = \int_{t_1}^{t_2} (J_{out}^- - J_{in}^-) dt + \int_{t_2}^{t_3} (J_{out}^- - J_{in}^-) dt \quad (14)$$

and if for the periods specified the following are true:

from $t_1$ to $t_2$, $J_{out}^- < J_{in}^-$ and, from $t_2$ to $t_3$, $J_{out}^- > J_{in}^-$ then the net can be adjusted to zero by appropriate scaling of the time intervals, i.e.

$$(J_{out}^- - J_{in}^-) \int_{t_1}^{t_2} = (J_{out}^- - J_{in}^-) \int_{t_2}^{t_3} \quad (15)$$

and, $$(t_2 - t_1)(J_{out}^- - J_{in}^-)_1 = (t_3 - t_2)(J_{out}^- J_{in}^-)_2 \quad (16)$$

where $J_{in}^-$ is constant but $J_{out}^-$ varies with the period, or, $$\frac{t_2 - t_1}{t_3 - t_2} = \frac{(J_{out}^- - J_{in}^-)_2}{(J_{out}^- - J_{in}^-)_1} \quad (17)$$

Thus, periodic changes in the rate of particle extraction without change in the polarity of the extracted particles could be used to maintain the charge neutrality of the sample.

Figure 3:
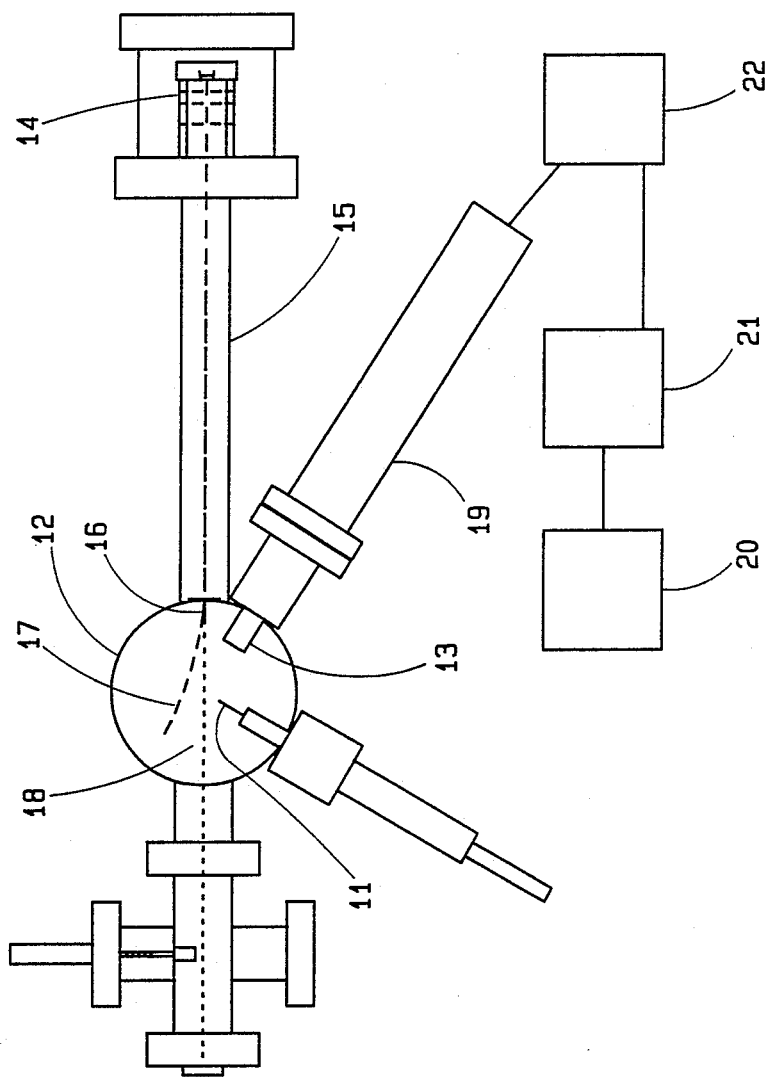
FIG. 3 is a schematic illustrating the apparatus of the present invention in combination with secondary ion mass spectroscopy apparatus.

An example of an apparatus that has been successfully used to practice the present invention is illustrated by FIG. 3. Ion source 14 provides sulfur hexafluoride anions which are focused and accelerated to an energy of 10 keV. As the anions travel through flight tube 15, some anions eject an electron becoming neutral and thus create a mix of negative and neutral particles. Deflection electrode 16 can be used to deflect the negative particles along a path indicated by dashed line 17 leaving only neutral particles to follow the path indicated by dotted line 18. The sample 11 of material to be tested is mounted so that it can be translated and rotated within sample chamber 12. An electric field for ion extraction is created using an 80% pass wire grid 13 located approximately 4 cm from the sample. Grid 13 is connected to voltage supply 20 which operates grid 13 at a potential between +200 and −200 volts. Voltage supply 20 is connected to voltage supply control means 21, which is programmable to control the duration and voltage of the voltage supply output. Particles extracted by grid 13 are analyzed by a quadrupole mass spectrometer 19 and data processing and display means 22. The apparatus of FIG. 3 can cause neutral, negative, or mixed neutral and negative primary particle beams to bombard sample 11, and can extract secondary charged particles of positive or negative charge with either a constant extraction field or a pulsed or alternating extraction field as illustrated in FIG. 1, or simply varying the extraction rate as illustrated in FIG. 2.

Polytetrafluorethylene (PTFE) and polyethylene terephthalate (PET) are highly nonconducting polymers that satisfy Equation 6 when subjected to a negative primary beam and negative secondary particle extraction. Samples of PTFE and PET were analyzed with the apparatus of FIG. 3 for 10 keV mixed negative ion and neutral particles of sulfur hexafluoride, neutral particles, and negative particles. Extraction voltage for the grid 13 was 188 V. Secondary particles were extracted by a constant electric field and by a square wave pulsed field, similar to FIG. 1, of 20 Hz with a negative to positive dwell ratio of 7/3. Pulsed extraction was found to produce greatly increased secondary ion collection efficiency compared to the constant field extraction.

Extraction voltage, frequency of extraction cycle, and dwell ratio are parameters which must be determined for each material sample for which the present invention is implemented. Generally, extraction voltage is arbitrarily specified to be within the range of design values of the apparatus used for particle extraction. Optimum or near optimum extraction cycle frequency and dwell ratio are experimentally determined by varying those parameters and observing charged particle collection efficiency. A wide range of adjustment for extraction cycle frequency and dwell ratio will allow for adjustment to create an acceptable charged particle collection efficiency for an arbitrarily specified extraction voltage and primary beam. Adjustment of the instrument to maximize efficiency is therefor reduced to dwell ratio and frequency adjustment. Continuously collecting data from extraction of alternating sign particles yields spectra of both positive and negative particles. A material may yield significantly more particles of one sign than the other and/or a constituent of a material may yield particles of only one charge sign. PTFE is an example of a material which yields a significantly greater number of negative F particles than positive F particles. A spectra created from only positive particles would not demonstrate the presence of fluorine. Creating spectra from particles of both charge signs will produce a more complete description of the material.

An alternative embodiment of the apparatus of FIG. 3 may include a voltage supply control means that can cooperate with data processing and display means 22 to analyze spectra of opposite charge sign individually. The voltage supply control means would identify the sign of the particles being extracted and the spectrometer would separate data due to each particle charge. The spectra of each charge sign could be individually displayed or combined.

Continuous collection of particles of alternate charge sign can also provide a time history of diagnostic processes. A metabolizing biospecimen could be analyzed by that technique to obtain time varying spectra of positive and negative particles.

Further, in SIMS the electronics of the secondary ion mass analyzer can be electronically switched to only sample when ions of the desired polarity are being attracted to the secondary ion optics after the alternating potential has sufficiently stabilized during each phase of the cycle. If the mass analyzer is a quadropole mass spectrometer (or any other charge polarity reversal tolerant mass analyzer) both positive and negative ion spectra can be sampled in a multiplexed fashion during periods of opposite potential polarities. Thus both the positive and negative secondary ion mass spectra would be collected at essentially the same time, eliminating the questions of sample aging or primary beam induced damage effects. This of course would require appropriate electronics for control of critical voltages and for properly sampling the ion signals.

Finally, prevention of charge accumulation will allow particle extraction for a long period of time so that the process may be monitored for a long period and separate collection of particles of opposite charge sign will provide the additional information about the material at all times during the process.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiments described explain the principles of the invention and practical applications and should enable others skilled in the art to utilize the invention in various embodiments and with various modifications as are suited to the particular use contemplated. It is intended that the scope of the invention be defined by the claims appended hereto.

The embodiments of this invention in which an exclusive property or privilege is claimed are defined as follows:

1. An apparatus for limiting charge accumulation on a surface of a sample from which charged particles created by bombardment by a beam are extracted comprising:

means for creating adjacent to said surface of said sample an electric field of predetermined polarity and magnitude;

means for monitoring charge accumulation on said surface of said sample while maintaining said electric field at constant polarity and magnitude;

means for experimentally determining periods of time during which extraction of desired secondary charged particles will cause said charge accumulation on said surface of said sample to change from one acceptable level to another, and means for combining said experimentally determined periods of time into successive periods of extraction such that after said successive periods of extraction charge accumulation on said surface of said sample will be at or near zero.

2. The apparatus of claim 1 wherein said desired secondary charged particles are of opposite charge sign.

3. The apparatus of claim 1 wherein said desired secondary charged particles are of common sign.

4. A method for limiting charge accumulation on the surface of a sample of material during bombardment of said sample by a primary beam and extraction of secondary charged particles including:

within the range of design values of the extraction apparatus, maintaining an alternating extraction voltage while experimentally determining the periods of time during which extraction of desired secondary charged particles will cause charge accumulation on the surface of said sample to change from one acceptable level to another, calculating charge flux into said sample for each said experimentally determined period of time, and for a plurality of desired particles, combining said experimentally determined periods of time into successive periods of extraction such that after said successive periods of extraction charge accumulation on said surface of said sample will be at or near zero.

5. The method of claim 4 wherein said sample of material is electrically non-conducting or poorly conducting.

6. The method of claim 5 further including varying the frequency of said alternating extraction voltage.

7. A method for limiting charge accumulation on the surface of a sample of material during bombardment of said sample by a primary beam and extraction of secondary charged particles including:

within the range of design values of the extraction apparatus, maintaining a constant extraction voltage while experimentally determining the periods of time during which extraction of desired secondary charged particles will cause charge accumulation on the surface of said sample to change from one acceptable level to another, calculating charge flux into said sample for each said experimentally determined period of time, and for a plurality of said desired secondary charged particles, combining said experimentally determined periods of time into successive periods of extraction such that after said successive periods of extraction charge accumulation on said surface of said sample will be at or near zero.

8. The method of claim 7 wherein said sample of material is electrically non-conducting or poorly conducting.

9. The method of claim 8 wherein said desired secondary charged particles are of one sign, either positive or negative.

10. The method of claim 9 further including varying the rate of extraction of said desired secondary charged particles.

11. The method of claim 8 wherein said desired secondary charged particles are of both positive and negative sign.

12. The method of claim 11 wherein said successive periods of extraction are foreshortened to provide near simultaneous extraction of secondary charged particles of positive and negative sign.

13. The method of claim 11 further including using data processing and display means to analyze the spectra of secondary charged particles of opposite charge sign individually.

* * * * *